(12) United States Patent
Chuo et al.

(10) Patent No.: US 10,782,282 B2
(45) Date of Patent: Sep. 22, 2020

(54) MICROORGANISM DETECTION SYSTEM

(71) Applicants: Chin-Hsing Chuo, Taichung (TW);
Chih-Meng Wang, Taichung (TW);
Chin-Yen Wang, Taichung (TW)

(72) Inventors: Chin-Hsing Chuo, Taichung (TW);
Chih-Meng Wang, Taichung (TW);
Chin-Yen Wang, Taichung (TW)

( * ) Notice: Subject to any disclaimer, the term of this patent is extended or adjusted under 35 U.S.C. 154(b) by 60 days.

(21) Appl. No.: 16/304,849

(22) PCT Filed: May 27, 2016

(86) PCT No.: PCT/CN2016/083579
§ 371 (c)(1),
(2) Date: Nov. 27, 2018

(87) PCT Pub. No.: WO2017/201723
PCT Pub. Date: Nov. 30, 2017

(65) Prior Publication Data
US 2019/0212321 A1  Jul. 11, 2019

(51) Int. Cl.
*G01N 33/487* (2006.01)
*B01L 3/00* (2006.01)
(Continued)

(52) U.S. Cl.
CPC .. *G01N 33/48735* (2013.01); *B01L 3/502761* (2013.01); *C12M 1/34* (2013.01); *G01N 21/00* (2013.01); *G01N 21/01* (2013.01); *G01N 33/50* (2013.01); *G01N 2021/0112* (2013.01); *G01N 2021/0131* (2013.01);
(Continued)

(58) Field of Classification Search
CPC .... B01L 3/502761; C12M 1/34; G01N 21/00; G01N 21/01; G01N 2021/0112; G01N 2021/0131; G01N 2021/0181; G01N 2021/0187; G01N 33/48735; G01N 33/50
See application file for complete search history.

(56) References Cited

U.S. PATENT DOCUMENTS 6,483,959 B1 * 11/2002 Singh ................. G01N 21/0303
385/12
7,267,797 B1 * 9/2007 Craighead .......... G01N 21/0303
422/50

(Continued)

FOREIGN PATENT DOCUMENTS

CN  102680276 A   9/2012
CN  204855390 U  12/2015
(Continued)

*Primary Examiner* — Sang H Nguyen
(74) *Attorney, Agent, or Firm* — Muncy, Geissler, Olds & Lowe, P.C.

(57) ABSTRACT

A microorganism detection system is provided for being disposed on a device to be detected which is closed, including a flow channel and a detection module. A fluid to be detected in the device to be detected flows in the flow channel. The detection module is disposed within the flow channel, including two slides, a microscopic module and at least one telescopic mechanism, each of the at least one telescopic mechanism is connected to one of the two slides and the flow channel. When the two slides approach each other, the fluid to be detected in a gap between the two slides is observable through the microscopic module.

9 Claims, 9 Drawing Sheets

(51) Int. Cl.
  *G01N 21/01* (2006.01)
  *G01N 21/00* (2006.01)
  *G01N 33/50* (2006.01)
  *C12M 1/34* (2006.01)

(52) U.S. Cl.
  CPC ............ *G01N 2021/0181* (2013.01); *G01N 2021/0187* (2013.01); *G01N 2021/0193* (2013.01)

(56) References Cited

U.S. PATENT DOCUMENTS

| | | | | |
|---|---|---|---|---|
| 8,821,799 | B2* | 9/2014 | Bassler | G01N 15/147 422/105 |
| 2002/0142477 | A1* | 10/2002 | Lewis | G01N 33/0031 436/151 |
| 2006/0092413 | A1* | 5/2006 | Kiesel | G01N 21/0303 356/301 |
| 2006/0223166 | A1* | 10/2006 | Wilding | B01F 15/0264 435/287.1 |
| 2009/0103091 | A1* | 4/2009 | Jones | G01N 21/45 356/342 |
| 2009/0161100 | A1* | 6/2009 | Minot | G02B 21/34 356/244 |
| 2010/0097605 | A1* | 4/2010 | Murakami | B01D 61/20 356/337 |
| 2011/0222062 | A1* | 9/2011 | Martini | G01N 21/05 356/417 |
| 2012/0015376 | A1* | 1/2012 | Bornhop | G01N 21/05 435/7.2 |
| 2013/0230912 | A1* | 9/2013 | Nukaga | B01J 19/0093 435/288.7 |
| 2015/0203369 | A1* | 7/2015 | Yanagawa | C02F 1/325 250/434 |
| 2016/0272933 | A1* | 9/2016 | Larimer | C12M 41/46 |

FOREIGN PATENT DOCUMENTS

| | | |
|---|---|---|
| CN | 105612001 A | 5/2016 |
| EP | 2980588 A1 | 2/2016 |
| GB | 2521885 A | 7/2015 |
| JP | 2015169549 A | 9/2015 |

* cited by examiner

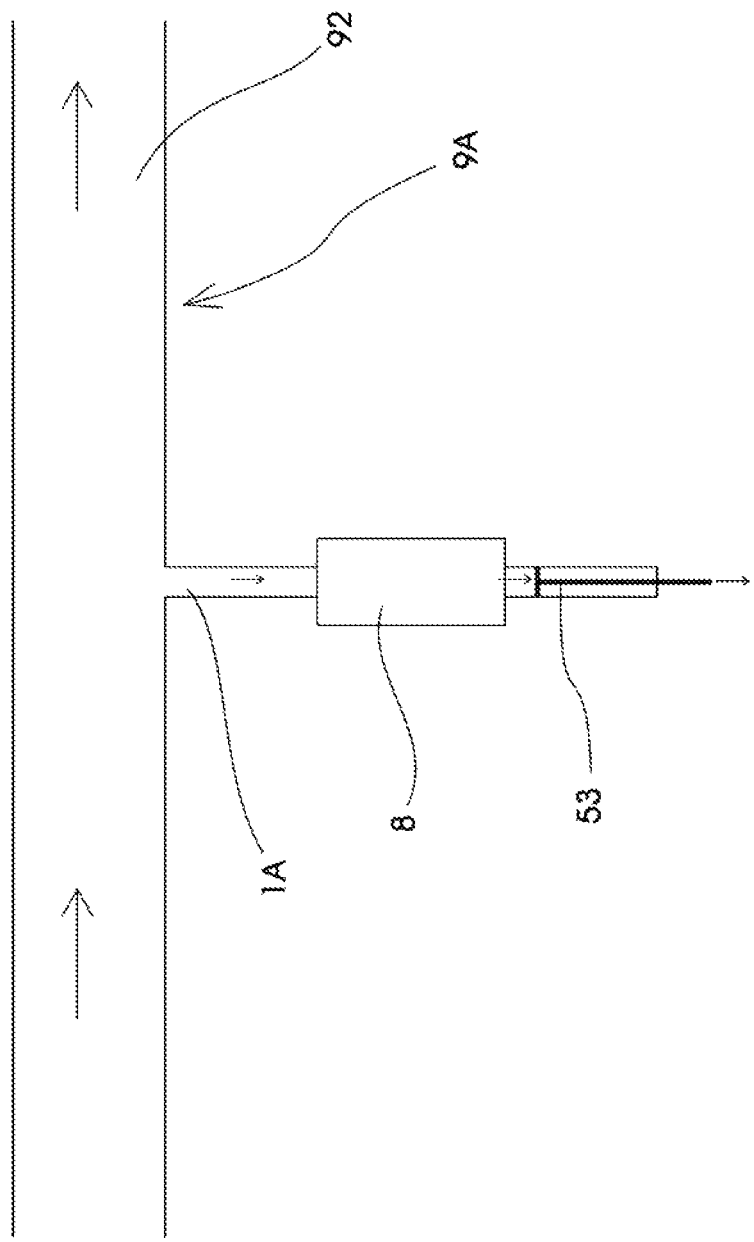

MICROORGANISM DETECTION SYSTEM

BACKGROUND OF THE INVENTION

Field of the Invention

The present invention relates to a detection system, and more particularly to a microorganism detection system.

Description of the Prior Art

Generally, when a user wants to examine an amount of the microorganism in an object to be detected (for example, food, water or bacterial culture solution), s/he needs to take a part of the object to be detected as a sample and place the sample on a microscopy device for examination so as to observe the amount of the microorganism in the object to be detected.

However, if the object to be detected is put in a closed-type device (for example, a bacterial culture tank or a food sterilization tank) which is separated from outside world, when the user wants to conduct detection, s/he has to open the closed-type device and take a small part of the object to be detected as a sample for detection. During the process of taking out the sample, microorganism from outside may accidentally enter the closed-type device and pollute the object to be detected in the closed-type device. In addition, the sample is detected outside, so it is hard to keep the sample from being polluted and from affecting the precision of the detection result.

The present invention has arisen to mitigate and/or obviate the afore-described disadvantages.

SUMMARY OF THE INVENTION

The major object of the present invention is to provide a microorganism detection system.

To achieve the above and other objects, a microorganism detection system is provided, for being disposed on a closed-type device to be detected, including a flow channel, a fluid to be detected in the device to be detected flowing in the flow channel; a detection module, disposed within the flow channel, including two slides, a microscopic module and at least one telescopic mechanism, the two slides disposed on two opposite sides of the flow channel, at least one of the two slides being light penetrable, the microscopic module being disposed on a side of the slide which is light penetrable and remote from the other of the two slides, each of the at least one telescopic mechanism being connected to one of the two slides and the flow channel; when the two slides approach each other, the fluid to be detected in a gap between the two slides is observable through the microscopic module.

Preferably, the microorganism detection system further includes at least one restricting member, the at least one restricting member is disposed on one of the two slides to restrict the two slides from approaching or moving relative to each other, and each of the at least one restricting member is a telescopic component; the microorganism detection system further includes at least one light emitting component, and each of the at least one light emitting component is disposed on a side of one of the two slides which is remote from the other of the two slides.

Preferably, the microorganism detection system further includes a compression device, the compression device is disposed within the flow channel to transport the fluid to be detected in the device to be detected from one of two ends of the flow channel to a place between the two slides, and the fluid to be detected is transported to the other of the two ends of the flow channel back to the device to be detected.

Preferably, a part of the flow channel is a square pipeline, the two slides are disposed respectively on two opposite sides of the square pipeline, the at least one telescopic mechanism is connected to at least one of the two slides and one of two sides of the square pipeline, and at least the two sides of the square pipeline on which the two slides are disposed are light penetrable.

Preferably, each of the at least one telescopic mechanism is a bellows tube which is connected to one of the two slides and one of the two sides of the square pipeline.

Preferably, the microscopic module includes a high magnification lens, and the device to be detected is a closed-type barrel or a closed-type pipeline.

Preferably, the microorganism detection system further includes an image capturing device, and the image capturing device is disposed on the microscopic module for capturing and recording a captured image which is projected from the gap between the two slides to the microscopic module.

Preferably, the microorganism detection system further includes a display unit, and the display unit is electrically connected to the image capturing device so as to send the captured image to the display unit to play.

Preferably, the microorganism detection system further includes a cloud database, the cloud database is in communication with the image capturing device, and the captured image captured by the image capturing device is sent to the cloud database.

Preferably, the microorganism detection system further includes a piston device, the piston device is disposed on one of two ends of the flow channel opposite to the device to be detected, the detection module is located between the piston device and the device to be detected, the piston device is for transporting the fluid to be detected in the device to be detected to the detection module through the flow channel, and the piston device is for transporting the fluid to be detected back to the device to be detected.

The present invention will become more obvious from the following description when taken in connection with the accompanying drawings, which show, for purpose of illustrations only, the preferred embodiment(s) in accordance with the present invention.

BRIEF DESCRIPTION OF THE DRAWINGS

FIG. 10 is a drawing showing a fifth preferred embodiment of the present invention in operation.

DETAILED DESCRIPTION OF THE PREFERRED EMBODIMENTS

Figure 1:
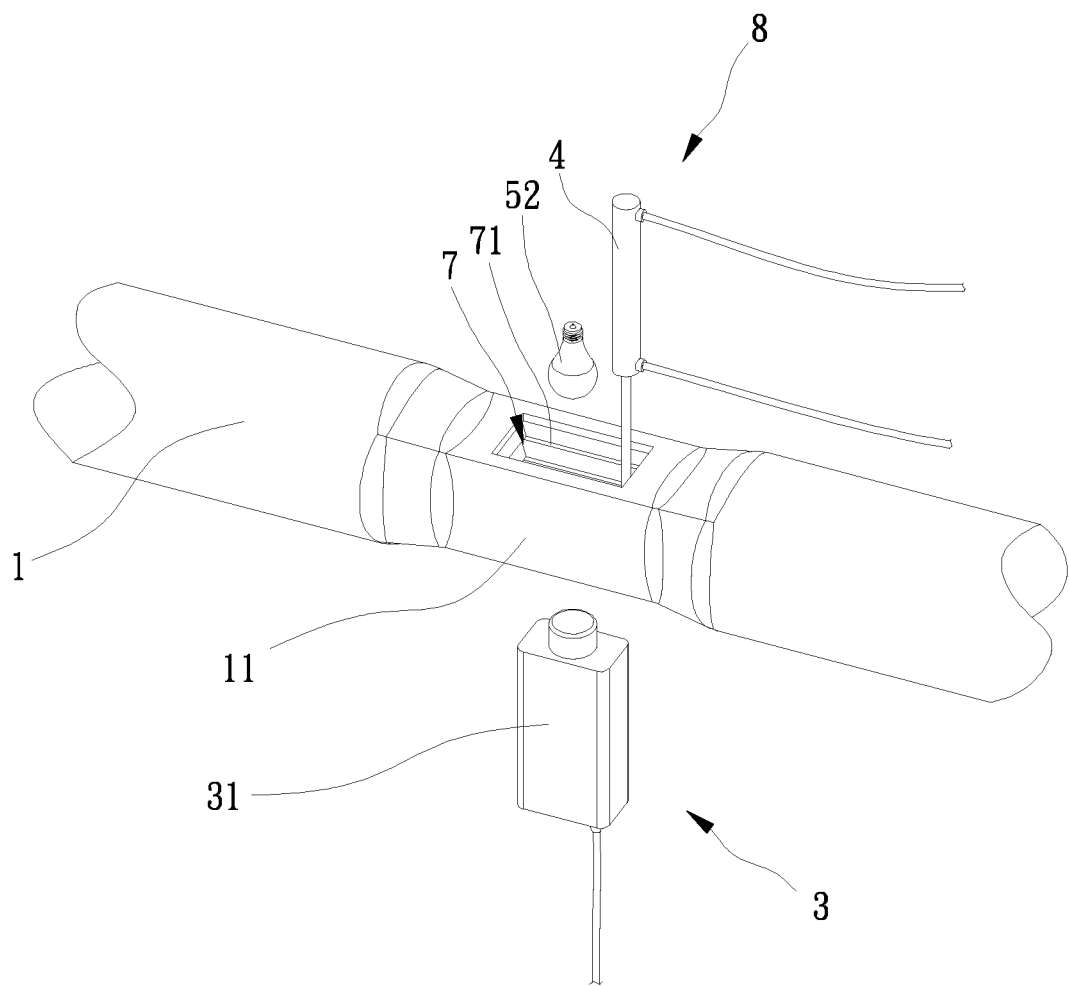
FIG. 1 is a stereogram of a first preferred embodiment of the present invention.
Figure 2:
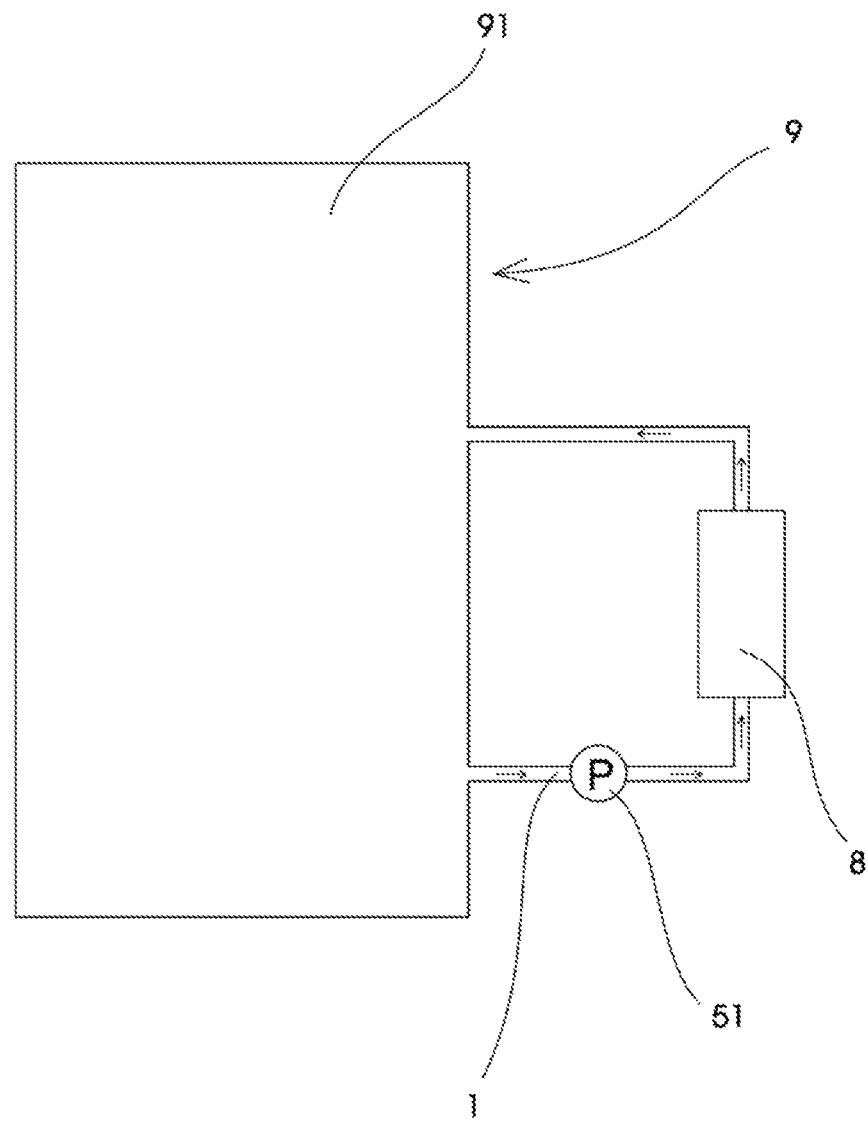
FIG. 2 is a drawing showing a structure of the first preferred embodiment of the present invention.
Figure 3:
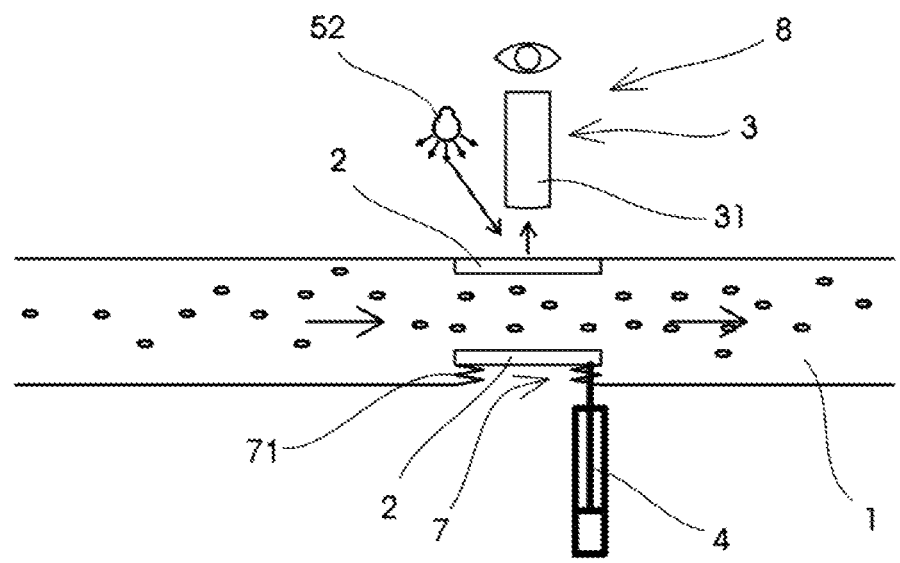
FIGS. 3 and 4 are drawings showing the first preferred embodiment of the present invention in operation.
Figure 4:
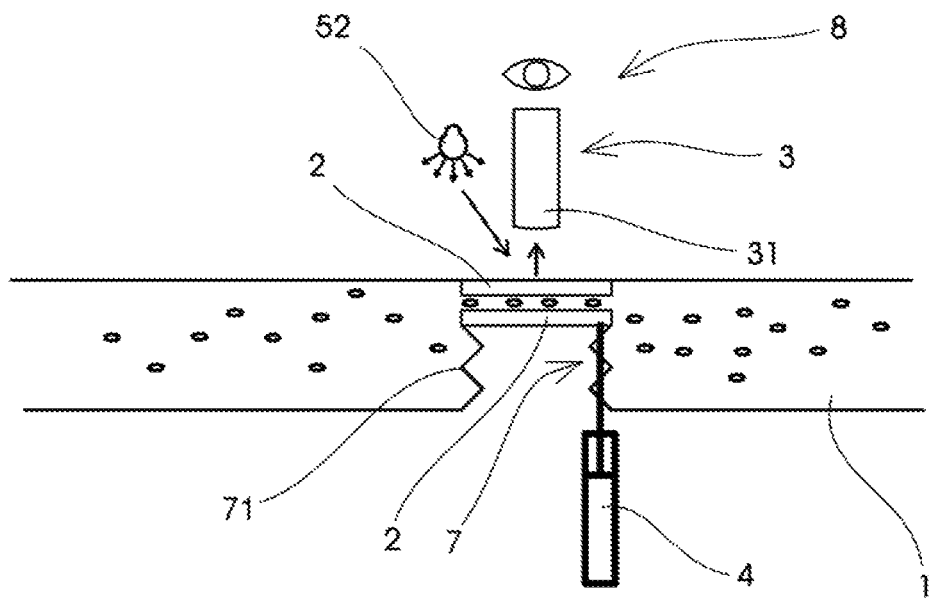

The present invention will be clearer from the following description when viewed together with the accompanying drawings, which show, for purpose of illustrations only, the preferred embodiment in accordance with the present invention.

Please refer to FIGS. 1 to 4 for a first preferred embodiment of the present invention. A microorganism detection system is provided for being disposed on a closed-type device to be detected 9, and the microorganism detection system includes a flow channel 1 and a detection module 8. The device to the detected 9 is a closed-type barrel 91 (for example, a cooker or a bacterial culture tank).

A fluid to be detected in the device to be detected 9 flows in the flow channel 1.

The detection module 8 is disposed within the flow channel 1 and includes two slides 2, a microscopic module 3 and at least one telescopic mechanism 7, the two slides 2 are disposed on two opposite sides of the flow channel 1, at least one of the two slides 2 are light penetrable, the microscopic module 3 is disposed on a side of the slide 2 which is light penetrable and remote from the other of the two slides 2 so that there is sufficient amount of light for a user to observe the fluid to be detected, and each of the at least one telescopic mechanism 7 is connected to one of the two slides 2 and the flow channel 1.

Specifically, when the two slides 2 approach each other, the fluid to be detected in a gap between the two slides 2 is observable through the microscopic module 3, and preferably, the microscopic module 3 includes a high magnification lens 31 so that the user can effectively observe microorganism through the microscopic module 3. Therefore, the user does not need to open the device to detected 9 to be communicable with outside and take a part of the fluid to be detected, s/he can precisely examine the fluid to be detected in the device to be detected 9 and effectively prevent the fluid to be detected in the device to be detected 9 from communicating with outside and being polluted.

In this embodiment, a part of the flow channel 1 is a square pipeline 11, the two slides 2 are disposed respectively on two opposite sides of the square pipeline 11, the at least one telescopic mechanism 7 is connected to at least one of the two slides 2 and one of two sides of the square pipeline 11, in this embodiment, the microorganism detection system includes one said telescopic mechanism 7, the telescopic mechanism 7 is disposed on one of the two slides 2 remote from the microscopic module 3, and preferably, at least the two sides of the square pipeline 11 on which the two slides 2 are disposed are light penetrable so that there is sufficient amount of light for the user to observe the fluid to be detected. It is to be noted that in this embodiment, the telescopic mechanism 7 is a bellows tube 71 which is connected to one of the two slides 2 and one of the two sides of the square pipeline 11 to smoothly move the slide 2 and to effectively close the square pipeline 11 to prevent the fluid to be detected from flowing out to outside.

Figure 5:
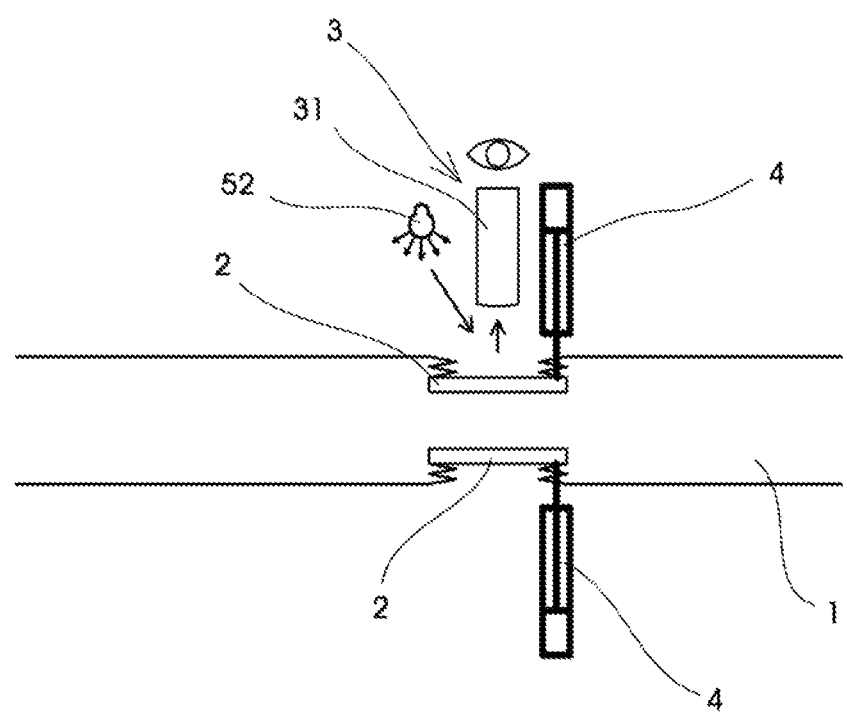
FIG. 5 is a drawing showing another mode of the first preferred embodiment of the present invention in operation.

Preferably, the microorganism detection system further includes at least one restricting member 4, the at least one restricting member 4 is disposed on one of the two slides 2 to restrict the two slides 2 from approaching or moving relative to each other, specifically, in this embodiment, the detection module 8 includes one said restricting member 4, the restricting member 4 is disposed on one of the two slides 2 remote from the microscopic module 3, the restricting member 4 is a telescopic component to move one of the two slides 2 toward or away from the other of the two slides 2 near the microscopic module 3, and in other embodiments, the two slides may have one said restricting member 4 (as shown in FIG. 5). Of course, in other embodiments, there may also be no restricting member, and the two slides can be moved manually.

It is to be noted that the microorganism detection system further includes a compression device 51, the compression device 51 is disposed within the flow channel 1 to transport the fluid to be detected in the device 9 to be detected from one of two ends of the flow channel 1 to a place between the two slides 2, and the fluid to be detected is transported to the other of the two ends of the flow channel 1 back to the device to be detected 9. In this embodiment, the compression device 51 is a pump, and the compression device 51 transports the fluid to be detected to a place between the two slides 2 through positive pressure. In other embodiments, the compression device 51 may also transport the fluid to be detected to a place between the two slides 2 through negative pressure, the compression device 51 can make the fluid to be detected in the device to be detected 9 flow smoothly through the flow channel 1 to the place between the two slides 2 for the user to examine via the detection module 8. In addition, the compression device 51 can transport the fluid to be detected from the other of two ends of the flow channel 1 back to the device to be detected 9 so as to ensure that the fluid to be detected which is detected by the detection module 8 is taken from the device to be detected 9 in real-time to elevate the examination precision.

Preferably, the microorganism detection system further includes at least one light emitting component 52 (in this embodiment, the light emitting component 52 is a LED light, and in other embodiments, the light emitting component 52 may be other types of light emitting component), and each of the at least one light emitting component 52 is disposed on a side of one of the two slides 2 which is remote from the other of the two slides 2. In this embodiment, there is one said light emitting component 52, the light emitting component 52 is disposed on one of two sides of the slide 2 near the microscopic module 3, and in other embodiments, and one of two sides of the two slides 2 has one said light emitting component 52.

Figure 6:
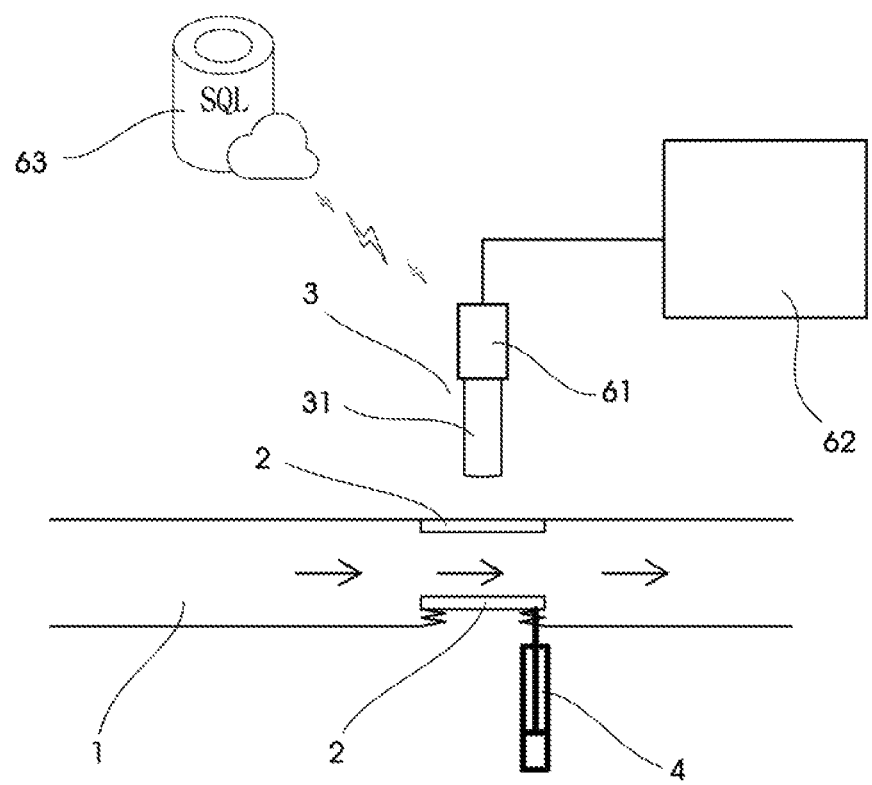
FIG. 6 is a drawing showing a second preferred embodiment of the present invention in operation.

Please refer to a second embodiment of FIG. 6, compared with the first embodiment, the microorganism detection system further includes an image capturing device 61, and the image capturing device 61 is disposed on the microscopic module 3 for capturing and recording a captured image which is projected from the gap between the two slides 2 to the microscopic module 3. In this embodiment, the image capturing device 61 is a CCD (Charge-Coupled Device) image sensor, and in other embodiments, the image capturing device 61 may also be a CMOS (Complementary Metal-Oxide-Semiconductor) image sensor.

In addition, in this embodiment, the microorganism detection system further includes a display unit 62 and a cloud database 63, and the display unit 62 is electrically connected to the image capturing device 61 so as to send the captured image to the display unit 62 to play; the cloud database 63 is in communication with the image capturing device 61, and the captured image captured by the image capturing device 61 is sent to the cloud database 63; therefore, the user needs to go to the microscopic module to observe and examine, through observing the captured image played by the display unit 62 or use a device (for example, a mobile phone or a computer) to connect the cloud database 63 to watch the captured image, so the user can know the status of the fluid to be detected, so it is more convenient for the user to examine in real-time. In other embodiments, the microorganism detection system may include only one of the display unit 62 and the cloud database 63 according to actual requirements.

Figure 7:
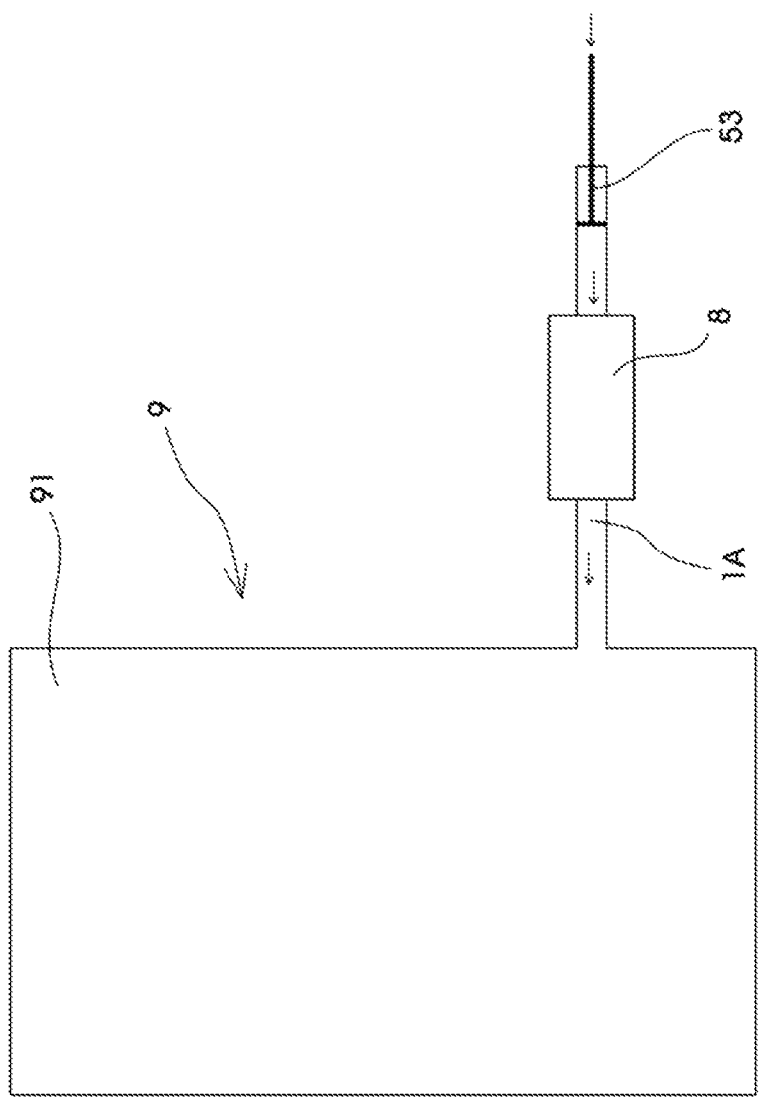
FIGS. 7 and 8 are drawings showing a structure of a third preferred embodiment of the present invention.
Figure 8:
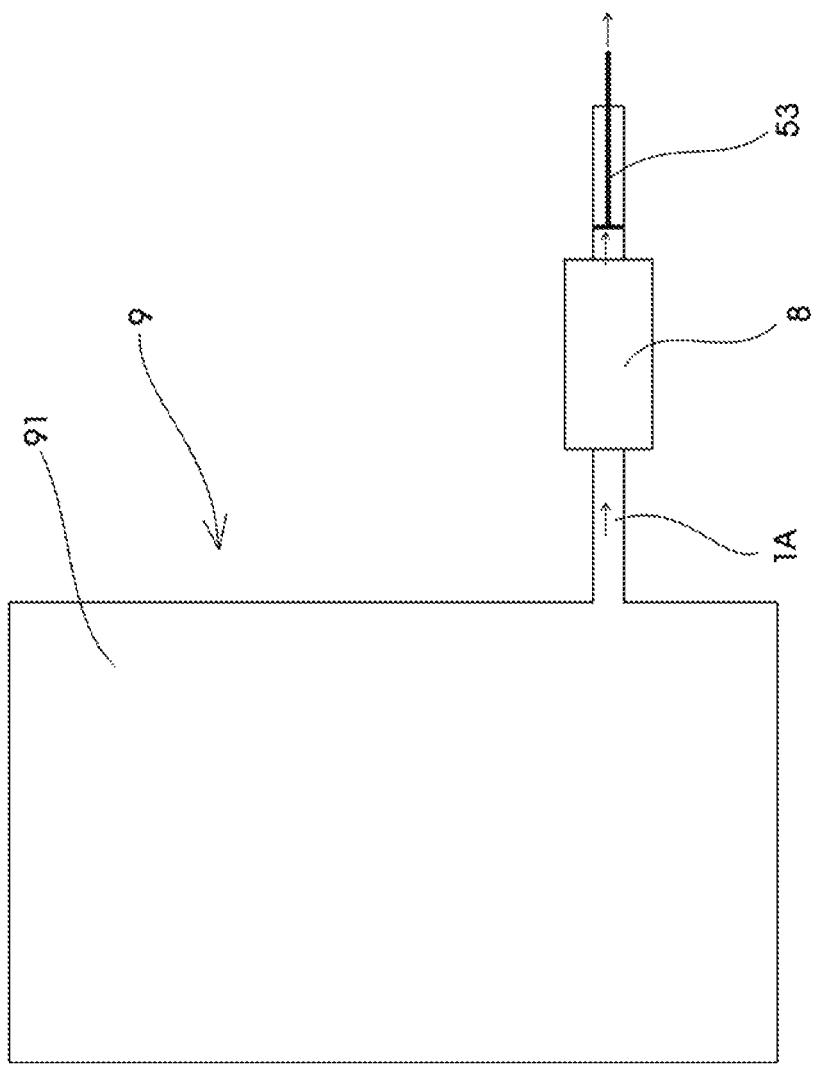

Please refer to a third embodiment of FIGS. 7 and 8, compared with the first embodiment, the microorganism detection system does not include the compression device but further includes a piston device 53, the piston device 53 is disposed on one of two ends of the flow channel 1A opposite to the device to be detected 9, the detection module 8 is located between the piston device 53 and the device to be detected 9, the piston device 53 is for transporting the fluid to be detected in the device to be detected 9 to the detection module 8 through the flow channel 1A, and the piston device 53 is for transporting the fluid to be detected back to the device to be detected 9. Therefore, in the third embodiment, it can be ensured that the fluid to be examined which is detected by the detection module 8 is taken from the device to be detected 9 in real-time to elevate the examination precision.

Figure 9:
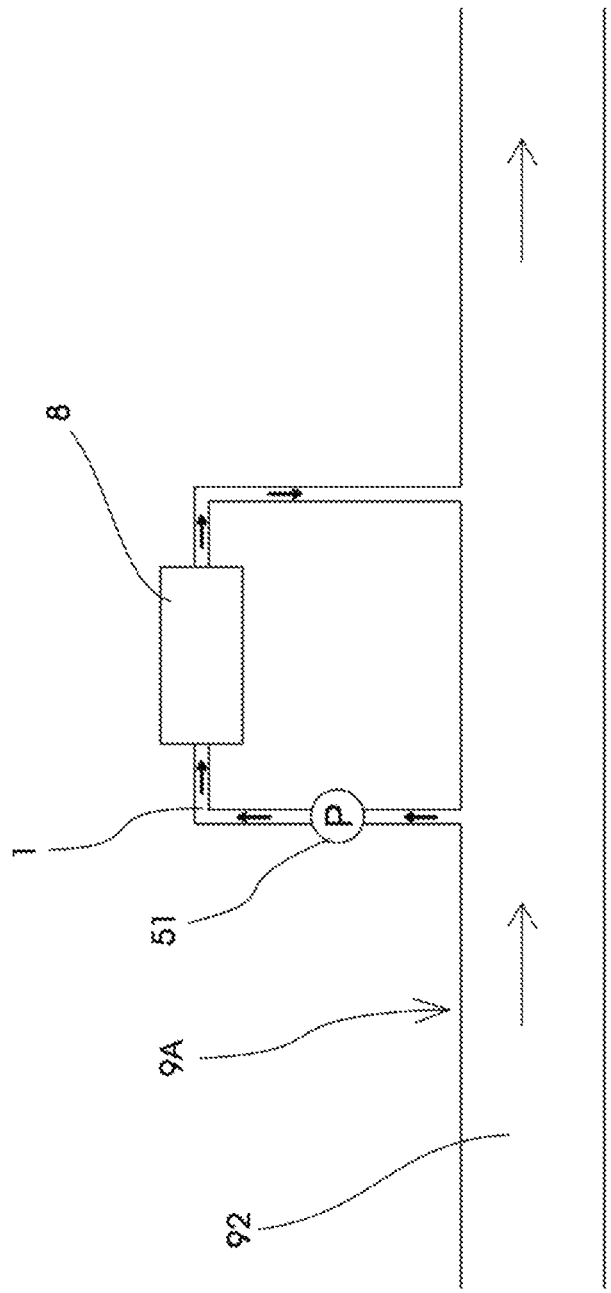
FIG. 9 is a drawing showing a fourth preferred embodiment of the present invention in operation.

Please refer to a fourth embodiment of FIG. 9, compared with the first embodiment, the microorganism detection system may be applied to the device to be detected 9A of a closed-type pipeline 92 (for example, a fluid transportation pipeline), the compression device 51A can make the fluid to be detected in the device to be detected 9A flow smoothly to the flow channel 1 and the detection module 8 to be detected in the detection module 8, and the fluid to be detected can be transported back to the device to the detected 9A through the other end of the flow channel 1. It is understandable that in a fifth embodiment of FIG. 10, compared with the fourth embodiment, the microorganism detection system does not include the compression device but further includes a piston device 53, the piston device 53 can transport the fluid to be detected in the device to be detected 9A to the detection module 8 through the flow channel 1A, and the piston device 53 is for transporting the fluid to be detected back to the device to be detected 9A.

Given the above, when the user wants to take out a part of the fluid to be detected, s/he does not need to open the device to be detected and make the device to be detected communicable with outside, the microorganism detection system can precisely examine the fluid to be detected in the device to be detected and effectively prevent the fluid to be detected in the device to be detected from being polluted.

In addition, the user does not go to the microscopic module to observe and detect, through observing the captured image played by the display unit or use a device to connect the cloud database to watch the captured image, the user can know the status of the fluid to be detected, so it is more convenient for the user to detect in real-time.

While we have shown and described various embodiments in accordance with the present invention, it should be clear to those skilled in the art that further embodiments may be made without departing from the scope of the present invention.

What is claimed is:

1. A microorganism detection system, for being disposed on a closed-type device to be detected, including:
   a flow channel, a fluid to be detected in the device to be detected flowing in the flow channel;
   two slides disposed on two opposite sides of the flow channel and disposed within the flow channel, at least one of the two slides being light penetrable;
   a high magnification lens, being disposed on a side of the slide which is light penetrable and remote from the other of the two slides; and
   at least one telescopic mechanism, each of the at least one telescopic mechanism being connected to one of the two slides and the flow channel;
   wherein when the two slides approach each other, the fluid to be detected in a gap between the two slides is observable through the high magnification lens; wherein the microorganism detection system further includes at least one restricting member, the at least one restricting member is disposed on one of the two slides to restrict the two slides from approaching or moving relative to each other, and each of the at least one restricting member is a telescopic component; the microorganism detection system further includes at least one light emitting component, and each of the at least one light emitting component is disposed on a side of one of the two slides which is remote from the other of the two slides.

2. The microorganism detection system of claim 1, wherein the microorganism detection system further includes a compression device, the compression device is disposed within the flow channel to transport the fluid to be detected in the device to be detected from one of two ends of the flow channel to a place between the two slides, and the fluid to be detected is transported to the other of the two ends of the flow channel back to the device to be detected.

3. The microorganism detection system of claim 1, wherein a part of the flow channel is a square pipeline, the two slides are disposed respectively on two opposite sides of the square pipeline, the at least one telescopic mechanism is connected to at least one of the two slides and one of two sides of the square pipeline, and at least the two sides of the square pipeline on which the two slides are disposed are light penetrable.

4. The microorganism detection system of claim 3, wherein each of the at least one telescopic mechanism is a bellows tube which is connected to one of the two slides and one of the two sides of the square pipeline.

5. The microorganism detection system of claim 1, wherein the device to be detected is a closed barrel or a closed pipeline.

6. The microorganism detection system of claim 5, wherein the microorganism detection system further includes an image capturing device, and the image capturing device is disposed on the high magnification lens for capturing and recording a captured image which is projected from the gap between the two slides to the high magnification lens.

7. The microorganism detection system of claim 6, wherein the microorganism detection system further includes a display unit, and the display unit is electrically connected to the image capturing device so as to send the captured image to the display unit to play.

8. The microorganism detection system of claim 6, wherein the microorganism detection system further includes a cloud database, the cloud database is in communication with the image capturing device, and the captured image captured by the image capturing device is sent to the cloud database.

9. A microorganism detection system, for being disposed on a closed-type device to be detected, including:
   a flow channel, a fluid to be detected in the device to be detected flowing in the flow channel;
   two slides disposed on two opposite sides of the flow channel and disposed within the flow channel, at least one of the two slides being light penetrable;
   a high magnification lens, being disposed on a side of the slide which is light penetrable and remote from the other of the two slides; and at least one telescopic mechanism, each of the at least one telescopic mechanism being connected to one of the two slides and the flow channel;

wherein when the two slides approach each other, the fluid to be detected in a gap between the two slides is observable through the high magnification lens;

wherein the microorganism detection system further includes a piston device, the piston device is disposed on one of two ends of the flow channel opposite to the device to be detected, the piston device is for transporting the fluid to be detected to flow in the flow channel and the piston device is for transporting the fluid to be detected back to the device to be detected.

\* \* \* \* \*